United States Patent
Winslow et al.

(10) Patent No.: US 6,972,331 B2
(45) Date of Patent: Dec. 6, 2005

(54) CARBOXY PYRROLE, PROCESS OF PREPARING AND USE AS PRECURSOR

(75) Inventors: Christopher D. Winslow, Charlottetown (CA); Philip E. Morris, Jr., Birmingham, AL (US)

(73) Assignee: BioCryst Pharmaceuticals, Inc., Birmingham, AL (US)

( * ) Notice: Subject to any disclaimer, the term of this patent is extended or adjusted under 35 U.S.C. 154(b) by 241 days.

(21) Appl. No.: 10/420,757

(22) Filed: Apr. 23, 2003

(65) Prior Publication Data

US 2004/0214840 A1 Oct. 28, 2004

(51) Int. Cl.[7] .................... C07D 487/04; C07D 207/34
(52) U.S. Cl. ......................... 544/280; 548/533
(58) Field of Search .......................... 544/280

(56) References Cited

FOREIGN PATENT DOCUMENTS

| WO | WO-99/19338 | 4/1999 |
| WO | WO-00/61783 | 10/2000 |

OTHER PUBLICATIONS

Mu III Lim, J. Org. Chem vol. 48, No. 6: Mar. 25, 1983 pp 780–788.*
Furneaus et al. Improved Syntheses of 3H,5H–Pyrrolo [3,2–d] pyrimidines, J. Org Chem, 1999, 64, 8411–8412, American Chemical Society.
Elliott et al. A Short, Facile Synthesis of 2–Amino–1, 5–dihydro–4H–pyrrolo[3,3,2–d]–pyrimidin–4–one (9–Deazaguanine), Tetrahedron Letters, vol. 37, No. 25, pp. 4339–4340, 1996 Copy right 1996 Elsevier Science Ltd.

* cited by examiner

*Primary Examiner*—Mark L. Berch
(74) *Attorney, Agent, or Firm*—Lodge & Hutz, LLP

(57) ABSTRACT

4-Oxo-4,5-dihydro-3H-pyrrolo[3,2-d] pyrimidine-7-carboxylic acid methyl ester and process for preparing are provided. The process for producing the 4-oxo-4,5-dihydro-3H-pyrrole[3,2-d]pyrimidine-7-carboxylic acid methyl ester comprises condensing 3-amino-1H-pyrrole-2,4-dicarboxylic acid dimethyl ester with formamidine acetate. The 4-oxo-4,5-dihydro-3H-pyrrole[3,2-d]pyrimidine-7-carboxylic acid methyl ester is useful as a precusor for providing 9-deaza-hypoxanthine, a key intermediate for producing certain PNP inhibitors.

22 Claims, No Drawings

CARBOXY PYRROLE, PROCESS OF PREPARING AND USE AS PRECURSOR

TECHNICAL FIELD

The present invention relates to 4-oxo-4,5-dihydro-3H-pyrrolo [3,2-d] pyrimidine-7-carboxylic acid methyl ester, which is especially useful for producing 3,5-dihydro-pyrrolo [3,2-d]pyrimidin-4-one (9-deazahypoxanthine), a key intermediate for producing certain inhibitors of the enzyme purine nucleoside phosphorylase (PNP). The present invention also relates to a process for preparing the 4-oxo-4,5-dihydro-3H-pyrrolo[3,2-d] pyrimidine-7-carboxylic acid methyl ester. In addition, the present invention relates to a process for producing 9-deazahypoxanthine.

BACKGROUND OF THE INVENTION

The enzyme purine nucleoside phosphorylase (PNP) catalyses the reversible cleavage of purine nucleosides to the purine base and ribose-1-phosphate. Several cases of a rare genetic disorder in which PNP is lacking have been reported in children. These children are found to be T-cell immuno-deficient while their B-cell immunity remained normal. This observation helped establish the relationship between PNP and T-cells and provided the impetus for the development of inhibitors of PNP which may be useful for the treatment of T-cell proliferative disorders. PNP functions as a salvage enzyme in the purine pathway. It is responsible for the reversible phosphorolysis of the ribonucleotides and 2'-deoxyriboncleotides of guanine, hypoxanthine, and related nucleotides to the free base and the phosphorylated sugar. Within intact cells, PNP normally acts in the phosphorolytic direction since the 6-oxopurines are further metabolized.

In children with enzyme deficiency, there is a low uric acid concentration since hypoxanthine and guanine catabolism is shut off and there are high inosine, guanosine, 2'-deoxyinosine, and dGuo nucleoside levels in plasma and urine. From the elevated nucleoside pool, only the elevated levels of dGuo have an inhibitory effect on T-cells. The elevated levels of dGuo become rapidly phosphorylated within these cells to 2'-deoxyguanosine monophosphate (dGMP) by their high level of 2'-deoxycytidine kinase (dCK). dGMP is further phosphorylated to its triphosphate (dGTP), which, in turn, shuts off DNA synthesis, preventing T-cell proliferation and eventually resulting in cell death. Only proliferating T-cells are impaired by this mechanism.

A number of PNP inhibitors are disclosed in U.S. Pat. No. 5,985,848 and PCT WO 99/19338, disclosures of which are incorporated herein by reference. 3,5-Dihydro-pyrrolo[3,2-d]pyrimidin-4-one (9-deazahypoxanthine) is a useful intermediate for the preparation of a key intermediate described in PCT WO 99/19338 as well as for the preparation of inhibitors of the enzyme purine nucleoside phosphorylase (PNP) described in U.S. Pat. No. 5,985,848.

A method for preparing 9-deazahypoxanthine from isoxazole has been disclosed in PCT WO 99/19338 and Furneaux, R. H., et al., *J. Org. Chem.*, 1999, 64, 8411. However, this method is not practical for large scale production. Specifically, the isoxazole starting material is not practical due to its relatively high cost and scant availability. The reported enamine intermediate is isolated as a viscous syrup containing a mixture of the E/Z isomers (used as the mixture) which is labor intensive. The pyrrole intermediate that is reported is not highly stable and must be purified by column chromatography prior to using in the next step. The final reported step involves condensation with formamidine acetate to produce 9-deazalhypoxanthine but with inconsistent yields and a product of varying quality. Also of some general background interest are PCT WO 00/61783 and Elliott et al. Tetrahedron Letters, Vol. 37, No. 25 pages 4339–4340, 1996.

Accordingly, it would be desirable to develop an alternative process for producing 9-deazahypoxanthine.

SUMMARY OF THE INVENTION

The present invention relates to 4-oxo-4,5-dihydro-3H-pyrrolo[3.2-d] pyrimidine-7-carboxylic acid methyl ester, which is useful as a precursor in synthesizing certain PNP inhibitors.

Another aspect of the present invention relates to a process for producing the 4-oxo-4,5-dihydro-3H-pyrrolo [3.2-d] pyrimidine-7-carboxylic acid methyl ester. The process comprises condensing 3-amino-1H-pyrrole-2,4-dicarboxylic acid dimethyl ester with formamidine acetate.

A still further aspect of the present invention relates to a process for producing 3,5-dihydro-pyrrolo[3,2-d] dipyrimidin-4-one which comprises saponifying and then decarboxylating 4-oxo-4,5-dihydro-3H-pyrrolo[3,2-d] pyrimidine-7-carboxylic acid methyl ester.

Other objects and advantages of the present invention will become readily apparent by those skilled in the art from the following detailed description, wherein it is shown and described preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description is to be regarded as illustrative in nature and not as restrictive.

DESCRIPTION OF BEST AND VARIOUS MODES FOR CARRYING OUT THE PRESENT INVENTION

The present invention relates to 4-oxo-4,5-dihydro-3,H-pyrrolo[3,2-d] pyrimidine-7-carboxylic acid methyl ester represented by the structure:

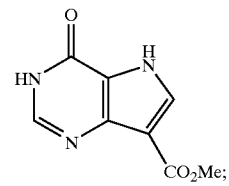

and a method for its preparation.

The 4-oxo-4,5-dihydro-3,H-pyrrolo[3,2-d] pyrimidine-7-carboxylic acid methyl ester can be prepared by condensing 3-amino-1H-pyrrolo-2,4-dicarboxylic acid dimethyl ester with formamidine acetate. The condensation is typically carried out employing elevated temperatures and in the presence of a diluent such as an alcohol. A typical alcohol is ethanol. The reaction can be carried out under reflux, if desired.

A preferred process for preparing the 3-amino-1H-pyrrolo-2,4-dicarboxylic acid dimethyl ester comprises reacting a dialkylaminomalonate or salt thereof with a 2-cyano-3-alkoxy-acrylic acid alkyl ester, and a methoxylating agent. A typical dialkylaminomalonate is diethylaminomalonate. A typical 2-cyano-3-alkoxy-acrylic acid alkyl ester is 2-cyano-3-ethoxy-acrylic acid ethyl ester.

The reaction can be carried out in the presence of a diluent such as an alcohol, an example of which being methanol. A typical methoxylating agent is sodium methoxide. During the admixing of the reactants, the temperature is typically maintained below about 45° C. The reaction is carried out under elevated temperatures, such as under reflux. After the reaction is completed, the reaction mass is cooled, such as to ambient temperature and neutralized with a weak acid such as acetic acid.

In addition, according to the present invention, the 4-oxo-4,5-dihydro-3H-pyrrolo[3,2-d] pyrimidine-7-carboxylic acid methyl ester can be used to produce 3,5-dihydro-pyrrolo[3,2-d] pyrimidin-4-one by saponification and then decarboxylation. The saponification can be carried out employing an alkali metal hydroxide such as sodium, potassium or lithium hydroxide with potassium hydroxide being preferred. The saponification can be carried out under elevated temperatures such as reflux. After the saponification is completed the reaction is cooled such as to ambient temperature, after which the reaction product is decarboxylated such as by adjusting the pH by adding a weak acid such as acetic acid.

The present invention can be illustrated by the following scheme employing preferred reactants for purposes of facilitating an understanding thereof.

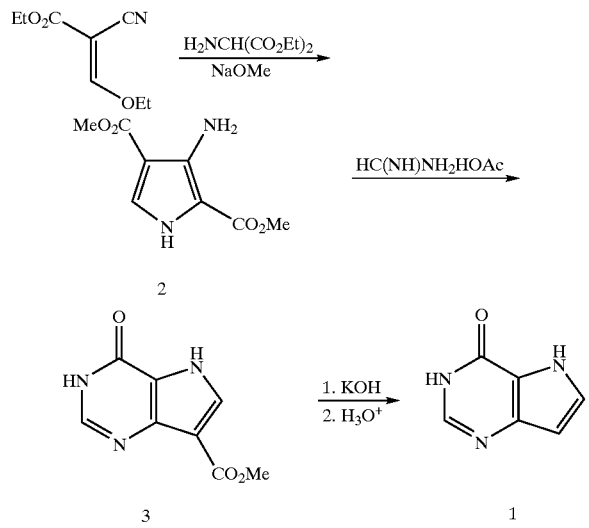

The following non-limiting examples are presented to further illustrate the present invention.

EXAMPLE 1

3-Amino-1H-pyrrole-2,4-dicarboxylic acid dimethyl ester (2)—To a methanol (16.6 L) solution containing diethylaminomalonate hydrochloride (1.877 kg) was added a solution of sodium methoxide (4.6 M, 5.745 L) in one-portion. 2-Cyano-3-ethoxy-acrylic acid ethyl ester (1.500 kg) was added over a 1-hour period such that the temperature was maintained less than 45° C. After the last addition, the mixture was heated at reflux for 4 hours and then cooled to ambient temperature. The mixture was neutralized with acetic acid (ca. 1 L) and then concentrated to a thick paste. Water (ca. 15 L) was added with stirring and the solid collected by vacuum filtration to give a tan solid, which was dried to give 1.2 kg (68.3%) of 2.

EXAMPLE 2

4-Oxo-4,5-dihydro-3H-pyrrolo[3,2-d]pyrimidine-7-carboxylic acid methyl ester (3)—A sample of the pyrrole 2 (1,189.5 g) was heated to reflux in ethanol (17.8 L) containing formamidine acetate (1,249.8 g) for 27 hours. To the hot solution was then added water (5 L) and the mixture filtered warm. The solid was dried in vacuo at 115° C. for 24 hours affording 707.73 g (61.1%) of 3 as a tan-solid.

EXAMPLE 3

3,5-Dihydropyrrolo[3,2-d]-pyrimidin-4-one (1)—A sample of the ester as prepared above (130.4 g) was heated to reflux with 11.2% aqueous KOH (1.35 L) for 40 hours. The mixture was cooled and carefully neutralized (ca. pH 6.5) with HOAc (162 mL) during which time $CO_2$ was evolved. The solid was collected by vacuum filtration, washed with saturated $NaHCO_3$ and triturated with $H_2O$ (400 mL) and. The solid was then dried in vacuo at 80° C. to give 67.6 g (74%) of 1 as an off-white solid.

The process of the present invention provides for good yields for each step of the process wherein each intermediate is a stable solid. In addition, the process of the present invention makes possible facile isolation of intermediates and the desired product. Moreover, the present invention does not require any chromatographic purifications as required by the prior art.

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill of knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also it is intended that the appended claims be construed to include alternative embodiments.

What is claimed as new and desired to be protected by Letters Patent of the United States is:

1. 4-Oxo-4,5-dihydro-3H-pyrrolo[3,2-d]pyrimidine-7-carboxylic acid methyl ester.

2. A process for producing 4-oxo-4,5-dihydro-3H-pyrrolo [3,2-d]pyrimidine-7-carboxylic acid methyl ester which comprises condensing 3-amino-1H-pyrrole-2,4-dicarboxylic acid dimethyl ester with formamidine acetate.

3. The process of claim 2 wherein the condensing is carried out under heat in the pressure of a diluent.

4. The process of claim 3 wherein the diluent is an alcohol.

5. The process of claim 4 wherein the alcohol is ethanol.

6. The process of claim 2 wherein the 3-amino-1H-pyrrole-2,4-dicarboxylic acid dimethyl ester is obtained by reacting a dialkylaminomalonate or salt thereof with a 2-cyano 3-ethoxy acrylic acid alkyl ester, and a methoxylating agent.

7. The process of claim 6 wherein the dialkylaminomalonate or salt thereof is diethylaminomalonate or salt thereof.

8. The process of claim 7 wherein the 2-cyano-3-alkoxy-acrylic acid alkyl ester is 2-cyano-3-ethoxy-acrylic acid ethyl ester.

9. The process of claim 6 wherein the 2-cyano-3-alkoxy-acrylic acid alkyl ester is 2-cyano-3-ethoxy-acrylic acid ethyl ester.

10. A process for producing 3,5-dihydropyrrolo[3,2-d]pyrimidine-4-one which comprises saponifying and then decarboxylating 4-oxo-4,5-dihydro-3H-pyrrolo[3,2-d]pyrimidine-7-carboxylic acid methyl ester.

11. The process of claim 10 wherein the saponifying is carried out employing an alkali metal hydroxide.

12. The process of claim 11 wherein the alkali metal hydroxide is KOH.

13. The process of claim 10 wherein the pH is adjusted by adding a weak acid for the decarboxylating.

14. The process of claim 13 wherein said acid is acetic acid.

15. The process of claim 10 wherein the 4-oxo-4,5-dihydro-3H-pyrrolo[3,2-d]pyrimidine-7-carboxylic acid methyl ester is obtained by condensing 3-amino-1H-pyrrole-2,4-dicarboxylic acid dimethyl ester with formamidine acetate.

16. The process of claim 15 wherein the condensing is carried out under heat in the pressure of a diluent.

17. The process of claim 16 wherein the diluent is an alcohol.

18. The process of claim 17 wherein the alcohol is ethanol.

19. The process of claim 10 wherein the 3-amino-1H-pyrrole-2,4-dicarboxylic acid dimethyl ester is obtained by reacting a dialkylaminomalonate or salt thereof with a 2-cyano-3-alkoxy-acrylic acid alkyl ester, and a methoxylating agent.

20. The process of claim 19 wherein the dialkylaminomalonate or salt thereof is diethylaminomalonate or salt thereof.

21. The process of claim 20 wherein the 2-cyano-3-alkoxy-acrylic acid alkyl ester is 2-cyano-3-ethoxy-acrylic acid ethyl ester.

22. The process of claim 19 wherein the 2-cyano-3-alkoxy-acrylic acid alkyl ester is 2-cyano-3-ethoxy-acrylic acid ethyl ester.

* * * * *